(12) United States Patent
Shah et al.

(10) Patent No.: US 7,544,301 B2
(45) Date of Patent: Jun. 9, 2009

(54) CITRATE-BASED DIALYSATE CHEMICAL FORMULATIONS

(75) Inventors: Dilip H. Shah, Buffalo Grove, IL (US); Todd Ing, Wilmette, IL (US)

(73) Assignee: HHD LLC, Manchester, NH (US)

( * ) Notice: Subject to any disclaimer, the term of this patent is extended or adjusted under 35 U.S.C. 154(b) by 457 days.

(21) Appl. No.: 10/921,677

(22) Filed: Aug. 19, 2004

(65) Prior Publication Data

US 2006/0037910 A1    Feb. 23, 2006

(51) Int. Cl.
*B01D 61/26* (2006.01)
*B01D 61/24* (2006.01)

(52) U.S. Cl. .................. 210/647; 210/321.71; 210/646; 424/600; 424/663; 424/678; 424/680; 424/681; 424/686; 424/717; 514/574; 604/29

(58) Field of Classification Search ............ 210/321.71, 210/646, 647; 424/600, 663, 678, 679, 680, 424/681, 686, 717; 514/574; 604/29

See application file for complete search history.

(56) References Cited

U.S. PATENT DOCUMENTS

| | | | |
|---|---|---|---|
| 3,441,135 A | 4/1969 | Lapple | 209/144 |
| 3,962,075 A | 6/1976 | Fialkoff et al. | 210/22 |
| 4,202,760 A | 5/1980 | Storey et al. | 210/22 |
| 4,292,227 A | 9/1981 | Michaels et al. | 260/29.6 |
| 4,326,955 A | 4/1982 | Babb et al. | 210/638 |
| 4,336,881 A | 6/1982 | Babb et al. | 206/525 |
| 4,489,535 A | 12/1984 | Veltman | 53/431 |
| 4,655,941 A | 4/1987 | Suzuki | 252/1 |
| 4,664,891 A | 5/1987 | Cosentino et al. | 422/269 |
| 4,756,838 A | 7/1988 | Veltman | 252/1 |
| 4,770,769 A | 9/1988 | Schael | 210/96.2 |
| 4,812,239 A | 3/1989 | Mills et al. | 210/647 |
| 5,032,615 A | 7/1991 | Ward et al. | 514/574 |
| 5,091,094 A | 2/1992 | Veech | 210/647 |
| 5,122,516 A | 6/1992 | Watanabe et al. | 514/23 |
| 5,244,568 A | 9/1993 | Lindsay | 210/87 |
| 5,252,213 A | 10/1993 | Ahmad et al. | 210/542 |
| 5,591,344 A | 1/1997 | Kenley et al. | 210/636 |
| 5,616,248 A | 4/1997 | Schal | 210/647 |
| 5,709,993 A | 1/1998 | Buturovic-Ponikvar | 435/2 |
| 5,788,099 A | 8/1998 | Treu et al. | 215/230 |
| 5,827,820 A | 10/1998 | duMoulin et al. | 514/2 |
| 6,139,754 A * | 10/2000 | Hartranft et al. | 210/739 |
| 6,251,437 B1 | 6/2001 | Fischbach | 424/489 |
| 6,566,402 B2 | 5/2003 | Warnock | 514/574 |
| 6,605,214 B1 * | 8/2003 | Taylor | 210/232 |
| 6,610,206 B1 | 8/2003 | Callan et al. | 210/646 |
| 2006/0226080 A1 * | 10/2006 | Degreve et al. | 210/647 |

FOREIGN PATENT DOCUMENTS

| | | |
|---|---|---|
| EP | 0 086 553 | 4/1987 |
| WO | WO 96/01118 | 1/1996 |
| WO | WO 98/10745 | 3/1998 |

OTHER PUBLICATIONS

Citrate Concentrate Material Safety Data Sheet (Dec. 1, 2000).*
Effect of citrate-containing dialysate on dialyzer reuse, HDCN: Review of Abstract (2000).*
Renal WEB Home Page, Citrasate/DRYalysate brochure (Mar. 2007).*
AAMI, "Concentrates foe hemodialysis", ANSI/AAMI RD61:2000, 2000, pp. 1-26.
Ahmad, et al., "Dialysate Made From Dry Chemicals Using Citric Acid Increases Dialysis Dose", *American Journal of Kidney Diseases*, vol. 35, No. 3, 2000, pp. 493-499.
Collart, et al., "Regional anticoagulation with sodium citrate: chronic utilization in the hemodialysis patient", *Nephrologie*, vol. 14, No. 3, 1993, pp. 151-154 (Abstract Only).
Flanigan, et al., "Regional Hemodialysis Anticoagulation: Hypertonic Tri-Sodium Citrate or Anticoagulant Citrate Dextrose-A", *American Journal of Kidney Dieseases*, vol. 27, No. 4, 1996, pp. 519-524.
Lohr, et al., "Regional Citrate Anticoagulation for Hemodialysis following Cardiovascular Surgery", *Am. J. Nephrol.*, vol. 8, 1988, pp. 368-372.
Lohr, et al., "Safety of Regional Citrate Hemodialysis in Acute Renal Failure", *American Journal of Kidney Diseases*, vol. 13, No. 2, 1989, pp. 104-107.
Meier-Kriesche, et al., "Unexpected severe hypocalcemia during continuous venovenous hemodialysis with regional citrate anticoagulation", *Am. J. Kidney Dis.*, vol. 33, No. 4, 1999, pp. e8 (Abstract Only).
Mehta, et al., "Regional citrate anticoagulation for continuous arteriovenous hemodialysis in critically ill patients", *Kidney International*, vol. 38, 1990, pp. 976-981.

(Continued)

*Primary Examiner*—John Kim
(74) *Attorney, Agent, or Firm*—McDonnell Boehnen Hulbert & Berghoff, LLP

(57) ABSTRACT

The present invention constitutes dialysate formulations that are suitable for use in preparing dialysate solutions for use in batch and/or proportioning systems and for improving dialysis efficiency by reducing or preventing clotting of the dialysis flow paths. The dialysate chemical formulations for one batch of dialysate comprise an acid concentrate stored in a first vessel, and a citrate-containing bicarbonate concentrate stored in a second vessel. The contents of the first and second vessels are emptied into a dialysate preparation tank and mixed with water to form a batch quantity of dialysate solution. Alternately, a dry acid and/or a dry citrate-containing base concentrates are dissolved separately in measured quantities of water to form liquid concentrates which are then used in conjunction with a proportioning machine to generate on-line a final dialysis solution stream.

23 Claims, No Drawings

OTHER PUBLICATIONS

Palsson, et al., "Regional citrate anticoagulation in continuous venovenous hemofiltration in critically ill patients with a high risk of bleeding", *Kidney International*, vol. 35, 1999, pp. 1991-1997.

Pinnick, et al., "Regional Citrate Anticoagulation For Hemodialysis in the Patient at High Risk For Bleeding", *The New England Journal of Medicine*, vol. 308, No. 5, 1983, pp. 258-261.

Pearl, et al., "Metabolic Alkalosis Due to Plasmapheresis", *The American Journal of Medicine*, vol. 79, 1985, pp. 391-393.

Tolwani, et al., "Simplified citrate anticoagulation for continuous renal replacement therapy", *Kidney International*, vol. 60, 2001, pp. 370-374.

Tu, et al., "Heparin-Free Hemodialysis with Citrate-Containing Dialysate in Intensive Care Patients", *Dialysis & Transplantation*, vol. 29, No. 10, 2000, pp. 620-624.

Van Der Meulen, et al., "Citrate anticoagulation and dialysate with reduced buffer content in chronic hemodialysis", *Clinical Nephrology*, vol. 37, No. 1, 1992, pp. 36-41.

Drukker, W., Parson, F.M., Maher, J.F. *Replacement of Renal Function by Dialysis*, Martinus Nijhoff Medical Division; The Hague, 1978, pp. 162-181.

Franz, H.E., *Blutreinigungsverfahren Technik und Klinik*, Georg Thieme Verlag Stuttgart; New York; 1990, pp. 129-152.

Baxter Healthcare Corporation, "Important Steps in Safely Using BIASOL™ During Dialysis Treatment", 1988.

Minntech Renal Systems Product Catalog, 2004, pp. 10-11.

Silverstein, et al., *Trans. Am. Soc. Artif. Intern. Organs*, vol. XXXV, 1989, pp. 22-25.

Baxter Healthcare Corporation Brochure, Biasol, Eri-Lyte, NatureLyte, and CentraLyte Formulations, pp. 1, 7-9 (1988).

Boen, et al., *Amer. Soc. Artif. Int. Organs*, vol. X, pp. 409-414, (1964).

Durigas, et al., *Handbook of Dialysis*, $2^{nd}$ ed., pp. 28-29, 44-45, 80-93, 404-405 (1994).

Schiwa Gmbh, Genius Dialysis System sales brochure, (1993-1995).

SERVIPAK® Home Dialysis Disposable Supplies brochure (1992).

Nissenson, et al., *Clinical Dialysis*, $2^{nd}$ Edition, 1990, pp. 50-51.

Sargent, et al., Proceedings of the Clinical Dialysis Transplant Forum, 1977, pp. 109-116.

\* cited by examiner

CITRATE-BASED DIALYSATE CHEMICAL FORMULATIONS

BACKGROUND OF THE INVENTION

A. Field of the Invention

This invention relates generally to chemical formulations that are used for the preparation of dialysate solutions, and more particularly to the distribution of chemicals into two dialysate concentrate formulations that are particularly suitable for use in preparing dialysate in both batch and proportioning dialysis systems. In the present context, the term "batch" refers to the quantity of dialysate constituents, that when mixed with the proper amount of water, forms enough dialysate solution sufficient for one complete dialysis session for single or multiple patients. The term "proportioning" refers to the traditional types of metering systems that are used to prepare dialysate, namely fixed-volume and dynamic proportioning systems. The two dialysate concentrate formulations are generally suitable for both batch preparation and on-line generation of dialysate as in traditional proportioning metering system after powder concentrate is dissolved to make a liquid concentrate.

B. Statement of Related Art

Kidneys help the body maintain a normal internal environment called homeostasis by ridding the body of excess fluids and metabolic waste products (toxins) as well as maintaining precise levels of glucose and electrolytes. When a person's kidneys fail because of disease or traumatic removal, excess fluid and toxic waste (uremic poisoning) accumulate in that person's body. This uremic poisoning eventually causes death unless the waste material is removed by some artificial means. Dialysis, including hemodialysis and peritoneal dialysis, is a treatment for patients that suffer from kidney failure. In hemodialysis, blood is pumped from the patient's body through an extracorporeal artificial kidney circuit, where blood-borne toxins and excess water are filtered out of the blood through a semipermeable dialyzer membrane into an electrolyte and plasma-resembling medium (i.e., dialysate). In peritoneal dialysis, the patient infuses a quantity of dialysate into the peritoneal cavity, and the peritoneal membrane acts as the semipermeable membrane. After a dwell period, the dialysate fluid is drained and a fresh supply of peritoneal dialysate is added to the peritoneal cavity.

A variety of concentrate formulations for preparing dialysis solutions used in hemodialysis or in peritoneal dialysis are known. See, for instance, U.S. Pat. Nos. 4,336,881; 4,489,535; and 4,756,838. These formulations vary not only with respect to specific constituents, but also with respect to the concentrations of these constituents. Generally, concentrate formulations include sodium chloride as the major constituent and potassium chloride, calcium chloride and magnesium chloride as minor constituents. If required by the patient, dextrose may also be included. Sodium acetate and/or sodium bicarbonate are also included as a buffer source to correct for metabolic acidosis. With acetate buffer, all of the constituents can be combined into a single concentrate. With bicarbonate buffer, two concentrates are necessary to prevent the precipitation of calcium and magnesium as carbonate salts.

Conventional two-part bicarbonate-based dialysis solutions are prepared by mixing an "acid" concentrate, a "base" (i.e., bicarbonate) concentrate and water. Normally the acid concentrate includes all of the acid (e.g., acetic acid), dextrose, calcium, magnesium, potassium and some portion of the physiologic requirement for sodium chloride whereas the base concentrate includes sodium bicarbonate and the balance of the required sodium chloride. In some commercial formulations of dialysate concentrates, the sodium chloride content of the base concentrate is zero. Since acetic acid is a liquid at room temperature, most of the acid concentrates using acetic acid are liquid products; whereas the base concentrates are produced both as powder and liquid concentrates. Many other combinations of acid and base concentrates that are commercially available are specific to the dialysis solution preparation methods and delivery equipment. For instance, the Aksys PHD® dialysis system (available from Aksys, Ltd., Lincolnshire, Ill., USA) uses a liquid acid concentrate and a dry base concentrate housed in two separate vessels. The sequential mixing of the two concentrates with purified water generates carbonic acid as reaction product of the acid with bicarbonate and results in a final dialysate having a pH within physiological limits but with sufficient acidity to prevent calcium and magnesium carbonate precipitation.

As noted above, kidney failure patients accumulate excess fluids and waste products in their body such as blood urea nitrogen (BUN) and creatinine. In fact, the reduction in blood level concentrations of these two substances is generally used to gauge the efficiency and overall effectiveness of dialysis. Often the efficiency of dialysis can be compromised by a number of factors, one of which is the blockage of dialyzer blood flow path by blood clots. Several attempts have been made to prevent or reduce clotting of dialyzer blood flow paths. For instance, Ward et al. U.S. Pat. No. 5,032,615 described the use of extra-corporeal infusion of anti-coagulants during dialysis. Ahmad et al. U.S. Pat. No. 5,252,213, issued Oct. 12, 1993, described the use of anti-coagulants in the dialysate formulations. The methods described in the patents of Ward et al. and Ahmad et al. require complicated monitoring or regulating systems to control the delivery of the anti-coagulants during dialysis or the use of chemical formulations that are inherently unstable and thus cannot be stored for prolonged time periods, respectively.

A number of dialysate delivery systems are available for preparing and delivering dialysate. Traditionally, dialysis systems were used for the preparation of large batches (e.g., 120 L or more) of dialysate. Single batches were prepared by adding dialysate constituents to a batch tank with a predetermined amount of purified water and mixing until dissolution occurred to yield a dialysate having a final desired concentration. A reference describing the preparation of a large quantity of dialysate off-line in 50 liter carboys in a factory-like facility is S. T. Boen et al., *Periodic Peritoneal Dialysis Using The Repeated Puncture Technique And An Automatic Cycling Machine*, Vol. X Trans. Amer. Soc. Artif. Int. Organs, 44. 409-414 (1964).

The two types of dialysis proportioning systems that are currently used to prepare dialysate include fixed-volume proportioning and dynamic (or servo-controlled) systems. For fixed-volume proportioning systems, fixed volumes of concentrate and water are mixed to form the final dialysate. Two pumps are used to dispense acid and bicarbonate concentrates while a third pump is used to meter water. The composition of the final dialysate is monitored by a conductivity sensor. Dynamic proportioning systems rely on conductivity monitoring to adjust the amount of acid and base concentrates that is mixed with water to yield a dialysate having a pre-set conductivity. These systems generally employ a second set of conductivity sensors for safety monitoring. The different approaches to preparing bicarbonate-containing dialysate resulted in a variety of proportioning ratios for the acid concentrates, base concentrates and water. Each proportioning ratio requires a particular set of acid and base concentrates. Some dialysis machines are designed for use with a single proportioning ratio while other machines use different proportioning ratios.

With the advent of on-line proportioning systems, dialysates can be prepared continuously on-line by combining water, which has been first purified by a separate water treatment system, with liquid concentrates of the dialysate constituents using a proportioning pump. A representative patent discussing this technique is the patent to Serfass, U.S. Pat. No. 3,441,135. An Association for the Advancement of Medical Instrumentation publication AAMI RD61:2000 describes four such proportioning systems where liquid acid concentrates and liquid bicarbonate concentrates are mixed on line with water to produce a final dialysate for use with hemodialysis therapy. These mix ratios are generally known as 35×, 36.83×, 45× and 36.1×. The details of different proportions are listed in Table 1(b). Recent advancements in automation technology and frequent on-line quality measurements have made it possible for use of proportioning systems in a home setting. New technology have made it possible to overcome the drawbacks of a proportioning systems and offer a more compact design particularly suitable for the home setting.

It is therefore an object of the invention to provide for the improved concentrate formulations of dialysate constituents that are suitable for preparation of batch as well as on-line generation of dialysate. This approach increases the efficiency of dialysis treatment by reducing clotting of blood. It is a further object of the invention to provide dialysate concentrate formulations that are particularly suited for automatic mixing of the constituents in a dialysate or concentrate tank. A further object of the invention is to provide concentrate formulations that assure patient safety, that are storage stable and will withstand temperature extremes when the concentrates are shipped from the location where they are formulated and bottled to the eventual destination.

SUMMARY OF THE INVENTION

The present invention relates to citrate-based dialysate formulations that are suitable for use in preparing on-line approach or batch quantities of dialysate, concentrate solutions, and kits and methods employing the same. The dialysate chemical formulations comprise a liquid or dry acid concentrate unit stored in a first vessel, and a liquid or dry citrate-containing bicarbonate concentrate unit stored in a second vessel. The contents of the first and second vessels are emptied into a dialysate preparation tank and mixed with water to form a batch quantity of dialysate solution. Alternately, the contents of the vessels can be be proportioned into a water stream for on-line generation of a dialysate solution. The mixing of chemicals and dilution with water is accomplished in an enclosed environment, under small pressure such that carbon dioxide formed remains dissolved in the solution. The present invention relates specifically to the dialysate chemical formulations; the vessels containing the chemicals and the machine that prepares the solution are not considered a part of the present invention per se.

In one embodiment of the invention, a dry citrate-containing base concentrate is provided. The dry citrate-containing base concentrate comprises citrate, bicarbonate and a salt, wherein the base concentrate upon mixing with an acid concentrate and a prescribed volume of water forms a final volume of a dialysis solution.

In one aspect of this embodiment of the invention, the dry base concentrate comprises: (a) bicarbonate in an amount sufficient to provide, in the final dialysate, a concentration ranging from about 15 to 50 mEq/L; (b) sodium in an amount sufficient to provide, in the final dialysate, a concentration ranging from about 125 to 150 mEq/L; (c) chloride in an amount sufficient to provide, in the final dialysate, a concentration ranging from about 80 to 130 mEq/L; and (d) citrate in an amount sufficient to provide, in the final dialysate, a concentration ranging from about 1 to 8 mEq/L, wherein the base concentrate upon mixing with an acid concentrate and a prescribed volume of water forms a final volume of a dialysis solution.

In another aspect of this embodiment of the invention, the base concentrate comprises sodium bicarbonate; sodium citrate; and sodium chloride, wherein the sodium bicarbonate and sodium citrate are present in molar ratios ranging from 50:1 to 15:8 and wherein sodium chloride is present in an amount sufficient to provide a sodium concentration ranging from 125 to 150 mEq/L in a final dialysate solution when the base concentrate and an acid concentrate are mixed in a prescribed volume of water.

In another embodiment of the invention, a kit is provided for preparing a dialysis solution. The kit comprises: (a) a container of a base component comprising a citrate, a bicarbonate and a salt; and (b) a container of an acid component comprising an acid selected from the group consisting of acetic acid, citric acid, sodium diacetate and lactic acid, wherein the addition of base concentrate and acid concentrate to a prescribed volume of water produces a final volume of a dialysis solution. Presently preferred formulations for the liquid acid concentrate and dry bicarbonate units are set forth in Tables 5 and 6, respectfully.

In another embodiment of the invention, a method is provided for making a dialysis solution. The method comprises: (a) providing a base concentrate comprising a citrate, bicarbonate and a salt; (b) providing an acid concentrate comprising an acid selected from the group consisting of acetic acid, citric acid, sodium diacetate and lactic acid; and (c) adding the base concentrate and said acid concentrate to a prescribed volume of water so as to produce said dialysis solution.

In another embodiment of the invention, a method is provided for making a dialysis solution. The method comprises: (a) providing a base concentrate comprising a citrate, bicarbonate and a salt; (b) providing an acid concentrate comprising an acid selected from the group consisting of acetic acid, citric acid, sodium diacetate and lactic acid; and (c) adding the base concentrate and said acid concentrate to a prescribed volume of water so as to produce said dialysis solution on a batch basis.

In one aspect of this embodiment of the invention, the base concentrate and acid concentrate are separately dissolved into water to form base and acid solutions. The base and acid solutions are then metered into a metered volume of water so as to produce said dialysis solution on-line on a continuous basis. The dissolution of the base and/or acid concentrates into water is necessary if the base and/or acid concentrates are in dry powder form.

These and other embodiments of the invention will become apparent in light of the detailed description below.

DETAILED DESCRIPTION OF THE PREFERRED EMBODIMENT

The assignee of the present invention has developed a daily hemodialysis machine that is particularly suitable for use in the home, nursing home, and limited care environment. The machine is described in the patent of Kenley et al., U.S. Pat. No. 5,591,344, issued Jan. 7, 1997, and is incorporated by reference herein. The machine prepares the dialysate solution a batch at a time, just prior to the start of the dialysis session. The dialysis chemicals are shipped to the machine site in vessels, each of which contains the batch quantity of either powdered or liquid dialysate chemicals. Thus, in one embodiment of the invention, the dialysate chemicals are used in conjunction with the machine described in the above Kenley et al. patent. A particularly preferred machine is the Aksys PHD® batch dialysis system which is commercially available from Aksys Ltd. The PHD® has been approved in the United States and in Europe for use in the home environment by dialysis patients.

To prepare the dialysate solution, dry dialysate chemicals in one batch quantity vessel, and liquid dialysate chemicals from one batch quantity vessel are dispersed into the dialysate tank. This process is described in detail in the above-referenced Kenley et al. patent.

In another embodiment of the invention, the dialysate chemicals are used in a dialysate proportioning system such as a fixed-volume or dynamic proportioning system.

The present invention contemplates dialysate concentrate formulations for preparing bicarbonate-based dialysate, consisting of a bicarbonate concentrate containing citrate and an acid concentrate which are stored in separate containers or vessels and mixed together in a dialysate suitable for hemodialysis or for peritoneal dialysis. The acid concentrates and bicarbonate concentrates of the invention are specially formulated to allow a physician to selectively tailor a dialysate formulation to a patient's particular health needs and to allow a patient to easily prepare batch size quantities of dialysate using a home dialysis machine described in Kenley et al. patent. The final dialysate preferably includes the following constituents (Table 1(a)) and is prepared in the following proportions (Table 1(b)):

TABLE 1(a)

Formulations Table for Final Dialysate for all HD and PD Solutions

| Constituent | Low | High | Units |
| --- | --- | --- | --- |
| Sodium | 125 | 150 | mEq/L |
| Bicarbonate | 15 | 50 | mEq/L |
| Citrate | 1 | 8 | mEq/L |
| Potassium | 0 | 5 | mEq/L |
| Magnesium | 0 | 3 | mEq/L |
| Calcium | 0 | 5 | mEq/L |
| Dextrose | 0 | 4250 | mg/dL |
| Chloride | 80 | 130 | mEq/L |
| Acetate | 0 | 8 | mEq/L |
| Lactate | 0 | 50 | mEq/L |

NB: HD = hemodialysis.
PD = peritoneal dialysis.

TABLE 1(b)

Volume and ratio ranges for dialysis components

| Constituent | Low | High | Units | Comment |
| --- | --- | --- | --- | --- |
| Acid Mix Ratio - Acid Concentrate and the sum of Base Concentrate and water | 1:34 | 1:136 | n/a | For Aksys Batch system (1:136) and other proportioning systems (1:34, 1:35.83, 1:44, 1:35.1). |
| Bicarbonate Mix ration - Base Concentrate and the sum of Acid Concentrate and water | 1:19.1 | 1:136 | n/a | For Aksys Batch system(1:136 for dry powder mixed directly) and other proportioning systems (1:27.6, 1:19.1, 1:25.1, 1:31.8). |
| Diluted Dialysate Solution Batch Size for a single treatment | 1 | 240 | liters | For Aksys Batch system and other proportioning systems utilizing batch mixing of powder concentrates |
| Diluted dialysis solution for proportioning systems | 50 | 1500 | mL/min | For most commercial proportioning systems |

The acid concentrate of the invention includes sodium chloride, dextrose and minor amounts of chloride salts of potassium, calcium and magnesium and an acid such as acetic acid, citric acid, sodium diacetate ($CH_3CO_2Na \cdot CH_3CO_2H$; CAS #000126-96-5), lactic acid or any other acid. Additionally, the corresponding salts of acetic acid (acetate), citric acid (citrate) or lactic acid (lactate) may be used.

As used herein, "chloride" refers to anionic chloride. Thus, the term "chloride" includes anionic chloride and the salt forms thereof, such as may be formed from chloride anion(s) and physiologically-acceptable cation(s). The term "chloride" is not intended to include compounds wherein the chloride atom is covalently bonded to, for example, a carbon atom in an organic molecule. Exemplary physiologically-acceptable cations include, without limitation, hydrogen ions (i.e., protons), metal cations, and ammonium cations. Metal cations are generally preferred, where suitable metal cations include, but are not limited to, the cationic forms of sodium, potassium, magnesium and calcium. Of these, sodium and potassium are preferred, and sodium is more preferred. A composition containing chloride salts may contain a mixture of physiologically-acceptable cations. A suitable chloride source may be any of hydrochloric acid, sodium chloride, potassium chloride, calcium chloride, magnesium chloride, ammonium chloride, or the like. In the preferred embodiment, chloride is in the form of sodium chloride.

As used herein, "acetate" refers to an acetate anion, in any form, including acetic acid and salts of acetic acid. Acetate is an organic, monocarboxylate with the formula $H_3CCO_2^-$. The acetate salt is composed of one or more acetate anions in association with one or more physiologically-acceptable cations. Exemplary physiologically-acceptable cations include, but are not limited to, protons, ammonium cations and metal cations, where metal cations are preferred. Suitable metal cations include, but are not limited to, sodium, potassium, magnesium and calcium, where sodium and potassium are preferred, and sodium is more preferred. For instance, the acetate source may be any of acetic acid, sodium acetate, sodium acetate trihydrate, sodium diacetate, potassium acetate, calcium acetate, calcium acetate monohydrate, magnesium acetate, magnesium acetate tetrahydrate, and the like.

Exemplary acetate compounds of the present invention include, but are not limited to, acetic acid, sodium acetate, sodium diacetate, sodium acetate trihydrate, potassium acetate, calcium acetate, calcium acetate monohydrate, magnesium acetate, and; magnesium acetate tetrahydrate. In the preferred embodiment, the acetate of the acid concentrate composition is present as acetic acid or sodium diacetate.

As used herein, "lactate" refers to a lactate anion, in any form, including lactic acid and salts of lactic acid. Lactate is an organic, monocarboxylate with the formula $H_3CCH(OH)CO_2^-$. A lactate salt is composed of one or more lactate anions in association with one or more physiologically-acceptable cations. Exemplary physiologically-acceptable cations include, but are not limited to, protons, ammonium cations and metal cations, where metal cations are preferred. Suitable metal cations include, but are not limited to, sodium, potassium, magnesium and calcium, where sodium and potassium are preferred, and sodium is more preferred.

Exemplary lactate compounds of the present invention include, but are not limited to, lactic acid, sodium lactate, potassium lactate, calcium lactate and magnesium lactate trihydrate. In one embodiment, the lactate of the acid concentrate composition is present in the form of lactic acid.

As used herein, "mEq/L" refers to the concentration of a particular dialysate component (solute) present in proportion to the amount of water present. More specifically, mEq/L refers to the number of milli-equivalents of solute per liter of water. Milli-equivalents per liter are calculated by dividing the moles per liter of solute by the number of charged species (groups) per molecule of solute, which is then divided by a factor of 1,000.

A preferred water of the invention is treated in order that it is essentially free of chemical and microbial contamination and at a minimum meets the purity requirements established by the Association for the Advancement of Medical Instrumentation (AAMI) for dialysate compositions. The water may also be referred to as treated water or AAMI-quality water. A monograph describing water treatment for dialysate, monitoring of water treatment systems, and regulation of water treatment systems is available from AAMI (Standards Collection, Volume 3, Dialysis, Section 3.2 Water Quality for Dialysis, 3 ed., 1998, AAMI, 3330 Washington Boulevard, Arlington, Va. 22201). In addition, all of the other components of the dialysate composition of the present invention are preferably at least at the level of United States Pharmacopoeia (USP)-grade purity, which is generally a purity of about 95%. The purity of the components is preferably at least about 95%, more preferably at least about 98%, and more preferably at least about 99%.

In order to facilitate the diffusion between blood and dialysate, it is desirable to maintain an osmotic gradient between the fluids by adding an osmotic agent to the dialysate. The presence of an osmotic agent in the peritoneal dialysate will encourage excess fluid and metabolic waste byproducts to flow from the blood and into the dialysate. A suitable osmotic agent for the dialysate composition is sugar. The sugar is preferably selected from glucose (e.g., dextrose), poly(glucose) (i.e., a polymer made from repeating glucose residues, e.g., icodextrin, made from repeating dextrose units), or fructose. While it is possible to make a dialysate with no sugar, if sugar is to be added to the dialysate composition, it is generally dextrose. It is further appreciated that any biocompatible, non-sugar osmotic agent that functions as an equivalent could be a viable substitute. The sugar is typically present in the acid concentrate in sufficient amounts to provide a concentration of 0 to 40 g/L on anhydrous basis in the final dialysate. In the preferred embodiment, glucose (i.e., dextrose monohydrate) is included in the acid concentrate in solubilized form to circumvent any potential dissolution problems in preparing the final dialysate formulation.

Table 2 lists the preferred constituents, concentration ranges and ionic strength for the acid concentrates. In the preferred embodiment of the invention, the acid concentrate is prepackaged in container, admixed with the bicarbonate concentrate in a dialysate preparation tank with a predetermined volume of water, then diluted to produce a 54.5 L batch dialysate using a home dialysis system such as the one described in the above referenced Kenley et al. patent.

TABLE 2

Acid concentrate range

| Constituent | Concentration (g/L) | Ionic Strength (mEq/L)* |
|---|---|---|
| NaCl | 80-159 | 10-20 ($Na^+$) |
| KCl | 0-41 | 0-4 ($K^+$) |
| $CaCl_2.2H_2O$ | 0-40 | 0.00-4.0($Ca^+$) |
| $MgCl_2.6 H_2O$ | 7-21 | 0.5-2.5 ($Mg^{++}$) |
| $CH_3COOH$ | 0-37 | 0-4.5 ($CH_3COO^-$) |
| Dextrose monohydrate | 0-376 | NA |
| Conductivity Range* | 2-3 mS/cm | NA |

*when diluted with water in a batch tank to a ratio of 1:135.6

The desired concentration of potassium, calcium and magnesium ions in the acid concentrate varies from patient to patient. Generally, the amount of potassium chloride is present in an amount ranging between about 0.00 g and about 41 g/L of acid concentrate. The amount of calcium chloride (dehydrate form, $CaCl_2.2H_2O$) generally ranges between about 0.00 and about 40 g/L of acid concentrate. The amount of magnesium chloride (hexahydrate form, $MgCl_2.6H_2O$) generally ranges between about 7 and about 21 g/L of acid concentrate. At the aforementioned concentrations, a stable acid concentrate is produced which can be shipped and stored for prolonged periods at a broad range of temperatures, including temperatures ranging between about −10 to −20 F, without freezing solid or precipitating out.

While the chloride salts of sodium, potassium, calcium and magnesium are preferred in practicing this invention, it will be understood by the practitioner that other water soluble physiologically acceptable salts of sodium, potassium, calcium and magnesium ions may be used to replace all or part of the corresponding chloride salts. Suitable, but non-limiting, salts include sulfates, carbonates, phosphates, acetates, lactates, and gluconates. If desired, hydrochloric acid, lactic acid, sodium diacetate or any other suitable acid may also be used to replace all or part of the acetic acid employed in the acid concentrate.

The bicarbonate base concentrate of the invention includes a dry admixture of sodium chloride, sodium bicarbonate, and citrate in a predetermined ratio. Table 3 lists the preferred constituents, concentration ranges, and ionic strength for the citrate-containing bicarbonate concentrates. Admixture of the bicarbonate concentrate batch unit with any of the acid concentrate batch units of the invention in an appropriate amount of water will result in a physiologically acceptable dialysate solution.

The base from which base concentrate is almost universally prepared in dialysis clinics is sodium bicarbonate, and this is the preferred base in the present compositions and methods. The bicarbonate concentrate in a dialysate is preferably from about 25 to 40 mEq/L. Optionally, the sodium bicarbonate in a base concentrate may be replaced, in part, with a different physiologically-acceptable base. The anionic portion of a suitable replacement for sodium bicarbonate may be, for example, carbonate, lactate, citrate and acetate. Accordingly, the base for a base concentrate may be selected from the salt forms of any of bicarbonate and, optionally, carbonate, lactate, citrate and acetate. Also present in the salt forms will be one or more physiologically-acceptable cations selected from sodium, potassium, calcium and magnesium. These salts and acids are electronically neutral, i.e., there are an equal number of negative and positive charges.

As used herein, "citrate" refers to a citrate anion, in any form, including citric acid (citrate anion complexed with three protons), salts containing citrate anion, and partial esters of citrate anion. Citrate anion is an organic tricarboxylate. Citric acid, which has been assigned Chemical Abstracts Registry No. 77-92-2, has the molecular formula $HOC(CO_2H)(CH_2CO_2H)_2$ and a formula weight of 192.12 g/mol. A citrate salt (i.e., a salt containing citrate anion) is composed of one or more citrate anions in association with one or more physiologically-acceptable cations. Exemplary physiologically-acceptable cations include, but are not limited to, protons, ammonium cations and metal cations. Suitable metal cations include, but are not limited to, sodium, potassium, calcium, and magnesium, where sodium and potassium are preferred, and sodium is more preferred. A composition containing citrate anion may contain a mixture of physiologically-acceptable cations.

A partial ester of a citrate anion will have one or two, but not all three, of the carboxylate (i.e., $-CO_2^-$) groups of citrate anion in an ester form (i.e., $-COOR$, where R is an organic group). In addition to one or two R groups, the partial ester of a citrate anion will include one or two physiologically-acceptable cations (so that the total of the R group(s) and cation(s) equals three). The R group is an organic group, preferably a lower alkyl.

The citrate is preferably in association with protons and/or metal cations. Exemplary of such citrate compounds are, without limitation, citric acid, sodium dihydrogen citrate, disodium hydrogen citrate, trisodium citrate, trisodium citrate dihydrate, potassium dihydrogen citrate, dipotassium hydrogen citrate, calcium citrate, and magnesium citrate. In one embodiment, the citrate is present in the base composition in the form of one or more of citric acid, sodium dihydrogen citrate, disodium hydrogen citrate, potassium dihydrogen citrate, or dipotassium hydrogen citrate. In a preferred embodiment, sodium citrate provides the source for the citrate anions. Sodium citrate may be in the form of a dry chemical powder, crystal, pellet or tablet. Any physiologically tolerable form of citric acid or sodium citrate may be used to introduce citrate anions to the bicarbonate composition. For instance, the citric acid or sodium citrate may be in the form of a hydrate, including a monohydrate.

Citrate has been previously recognized to be able to function as an anti-coagulant in the bloodstream by binding calcium. It has been successfully used for regional anticoagulation in hemodialysis. Concentration of citrate (up to 1.6 moles/L) are infused on the arterial side before the dialyzer and then additional calcium and magnesium salts are infused post dialyzer to keep ionized calcium and magnesium balance in the blood stream. Also, citrate concentrations as high as 47 mEq/L are used in whole blood and plasma collection bags to preserve the blood for transfusion and prevent it from clotting. The blood and plasma collected along with highly concentrated citrate is transfused to patients. Typically, plasma donation introduces 3.2 grams of sodium citrate in the donor's blood stream. This amount of citrate metabolizes rapidly in the body and converts to bicarbonate, which is the natural buffer in the blood stream. Accordingly, the citrate concentration of the bicarbonate concentrate should be selected in view of its anti-coagulation properties. Unless other measures are taken, the citrate concentration should not exceed about 8 mEq/L, and is preferably not more than about 4 mEq/L when diluted in the final dialysate solution. When citrate concentrations of higher than 8 mEq/L are employed, the magnesium and/or calcium concentration of the dialysate composition must be increased to compensate for calcium and magnesium ions lost to reaction with citrate. This can involve complicated physiological balancing of ionized calcium and magnesium such that higher than 8 mEq/L of citrate is not recommended in the dialysate solutions.

When sodium citrate is used as the citrate source, the bicarbonate concentrate may exist as a dry chemical mixture of salts. Since sodium citrate does not react with bicarbonate, citrate and bicarbonate salts do not need to be physically separated. These salts may be formed into tablets or pellets if desired. If citric acid or disodium citrate is used as the citrate source, the citrate is physically separated from the bicarbonate to avoid chemical reaction. Thus, in one embodiment of the invention, the bicarbonate base and citrate are physically separated in a vessel using sodium chloride salt as a barrier layer. For instance, the reagents can be layered by adding sodium bicarbonate, followed by sodium chloride and lastly citrate. In one aspect of this embodiment, the citrate may be tabletized or pelletized to reduce the surface area available for contact with bicarbonate.

In another embodiment, the citrate may be placed in a subcontainer and then the subcontainer is placed in the vessel containing the remaining bicarbonate concentrate constituents. In one aspect of this embodiment, the subcontainer may be porous, e.g., a filter bag, which physically separates the citrate from the bicarbonate but allows water, during the mixing process, to enter the subcontainer to dissolve the citrate. In another aspect of this embodiment, the subcontainer is non-porous, e.g., a sealed plastic bag, which is pierced just prior to mixing.

In yet another embodiment, the subcontainer is a compartment within the vessel that is created by the use of a physical barrier such as a plastic or paper membrane. The physical barrier separates the citrate from the bicarbonate and is ruptured just prior to mixing. For instance, sodium bicarbonate and sodium chloride is added to the vessel and sealed using a paper or plastic membrane insert. Citrate is then added to the vessel. In another embodiment, the citrate is tabletted or pelletized and a discrete number of tablets or pellets is added to the vessel to form the base concentrate. The citrate tablets or pellets may be coated with an isolation coating, i.e., dextrose or sodium chloride, to shield it from contact with the bicarbonate. The citrate may be present as a single or multiple tablets or pellets. In practicing this invention, it is preferred that the dry base concentrate is prepared with citrate pellet(s) or tablet(s) which is separated from the bicarbonate base via a sodium chloride salt layer.

In another embodiment of the invention, the base concentrate includes sufficient amounts of citrate, sodium, chloride and bicarbonate to produce, in the final dialysate, a citrate concentration ranging from about 2.5 to 4 mEq/L; sodium in an amount ranging from about 123 to 127 mEq/L; chloride in an amount ranging from about 84 to 89 mEq/L; and bicarbonate in an amount ranging from about 30 to 36.5 mEq/L. See Table 3. In one aspect of this embodiment, the base concentrate comprises sufficient amounts of bicarbonate, sodium, chloride and citrate to provide, in the final dialysate, 36.5 mEq/L of bicarbonate; 127 mEq/L of sodium; 88 mEq/L of chloride; and 2.5 mEq/L of citrate. In another aspect of this embodiment, the base concentrate comprises sufficient amounts of bicarbonate, sodium, chloride and citrate to provide, in the final dialysate, 31.5 mEq/L of bicarbonate; 123 mEq/L of sodium; 89 mEq/L of chloride; and 2.5 mEq/L of citrate. In yet another aspect of this embodiment, the base concentrate comprises sufficient amounts of bicarbonate, sodium, chloride and citrate to provide, in the final dialysate, 36.5 mEq/L of bicarbonate; 123 mEq/L of sodium; 84 mEq/L of chloride; and 2.5 mEq/L of citrate. In another aspect of this embodiment, the base concentrate comprises 35 mEq/L of bicarbonate; 127 mEq/L of sodium; 88 mEq/L of chloride; and 4 mEq/L of citrate.

TABLE 3

Citrate-containing bicarbonate powder range

| Constituent | Strength | Units |
|---|---|---|
| Sodium (Na$^+$) | 123-127 | (mEq/L)* |
| Bicarbonate (HCO$_3^+$) | 30.0-36.5 | (mEq/L)* |
| Chloride (Cl$^-$) | 84-89 | (mEq/L)* |
| Citrate (C$_6$H$_4$O$_7$) | 2.5-4 | (mEq/L)* |
| NaCl | 267.5-283.5 | Gms per bottle |
| NaHCO$_3$ | 137.4-167.1 | Gms per bottle |
| Sodium Citrate | 8.7-14.0 | Gms per bottle |
| Conductivity Range | 10.5-12.7 | mS/cm |

*when diluted in a batch tank with 54.5 liters of water

An embodiment of the present invention for commercially available proportioning systems (per AAMI RD61:2000) is listed in Table 4 below. The acid and bicarbonate concentrates can be supplied in dry forms. Table 4 below depicts the acid concentrate: bicarbonate concentrate: water ratios for the various proportioning dialysate generating systems that are commercially available at present. As an example in table 4 below, a citrate concentration of 4 mEq/L, an acetate concentration of 4 mEq/L and a bicarbonate concentration of 31 mEq/L can provide a final total base concentration of 39 mEq/L. It should be realized that these concentrations will differ greatly when the bicarbonate to citrate molar ratio is varied from 50:1 to 15:8 as listed in Table 1(a) above and that the ratios for different proportioning machines do vary. The base concentrates are generally used within 24 hours after a liquid container has been opened or a dry package has been dissolved in water.

ages for each dialysis session, each unit containing a predetermined quantity of the various constituents such when combined with water results in a batch dialysate formulation having the desired concentrations of constituents. The unit dosage forms are preferably contained in prepackaged sealed unit dose containers or vessels such as the one described in the Treu et al. U.S. Pat. No. 5,788,099, issued Aug. 8, 1998, which is incorporated by reference herein in its entirety and can be assembled in kit form for one or more dialysis sessions. The vessels described in the Treu et al. patent are especially designed for patient use and are particularly advantageous for use in conjunction with the home dialysis machine described in the above-referenced Kenley et al. patent. However, the present dialysate chemical formulation invention is of course applicable to other vessel designs and machines. In an embodiment of the invention, vessels can be prepackaged as a kit that includes a container of a dry base component comprising a citrate, a bicarbonate and a salt; and a container of a liquid acid concentrate comprising an acid selected from the group consisting of acetic acid, citric acid, sodium diacetate lactic acid or any other acid wherein the addition of base concentrate and acid concentrate to a prescribed volume of water produces a final volume of a dialysis solution. A set of instructions for using the components would also be included in the kit.

There are a number of advantages that can be obtained from the distribution of chemicals in the two concentrate bottles according to the present invention. First, patient safety is assured in batch or proportioning systems that employ the concentrates of the present invention. For instance, the conductivity of the acid concentrate of the invention generally ranges between about 2-3 mS/cm while the bicarbonate concentrate of the invention generally ranges about 10.5 to 12.7 mS/cm. The combined conductivity ranges between about

TABLE 4

Example of proportioning system compositions

| Symbol* for proportioning systems - except Aksys | Mix Ratio = sum of acid, bicarb and water | Acid concentrate | Bicarb concentrate | Water | g/L of sodium bicarbonate in base concentrate | g/L of sodium citrate in base concentrate | g/L of acetic acid in acid concentrate | Ratio of sodium bicarbonate to sodium citrate in g/g |
|---|---|---|---|---|---|---|---|---|
| Square | 35 | 1 | 1.23 | 32.77 | 74.4 | 9.8 | 8.4 | 7.60 |
| Circle | 36.83 | 1 | 1.83 | 34 | 59.2 | 6.9 | 8.8 | 8.55 |
| Triangle | 45 | 1 | 1.72 | 42.28 | 72.5 | 9.0 | 10.8 | 8.05 |
| Diamond | 36.1 | 1 | 1.1 | 34 | 77.0 | 11.3 | 8.7 | 6.82 |
| Aksys | 136.6 | 1 | 10.0 | 125.6 | 40.0 | 4.7 | 32.8 | 8.54 |

*Adapted from Association for the Advancement of Medical Instrumentation (AAMI) RD61: 2000

The present invention relates to the use of citrate as a base, mole for mole, in the place of bicarbonate or acetate. Thus, for a patient currently requiring 39 mEq/L of bicarbonate along with 4 mEq/L of acetate in the final dialysate, the patient can be provided instead with 35 mEq/L of bicarbonate, 4 mEq/L of citrate and 4 mEq/L of acetate. In another embodiment, for example, 33 mEq/L of bicarbonate, 5 mEq/L of citrate and 3 mEq/L of acetate can be used. The selection of these bases will depend on the citrate and acetate tolerances of the patient. Such tolerances are determined by the treating physician.

In practicing this invention, both the acid concentrate and the bicarbonate concentrate of the invention are preferably in the form of physically discrete units suitable as unitary dos- 12.5 to 15.7 mS/cm. If two acid concentrate bottles are accidentally mixed, the final conductivity will be below 12.8. Similarly, accidental mixing of two bicarbonate concentrate bottles will result in a combined conductivity that exceeds 15.7 mS/cm. In either case, the systems that measure conductivity of a dialysate solution prior to initiation of the dialysis procedure will not start the dialysis procedure. Also, machines are generally designed to compare the actual conductivity with the prescribed one within +/−5%. If the contents of any of the bottle did not mix in the final dialysate solution, the loss of conductivity will be indicated and dialysis procedure will also be halted.

Ordinarily, the conductivity level of dialysate solution resulting from the mixing of vessels containing the acid and bicarbonate concentrates in the batch tank proportioning system would fall within the expected aforementioned range. No safety alarm will sound and the dialysis session would proceed uneventfully. Inadvertent mixing of two like vessels, e.g., two acid concentrate vessels or two bicarbonate concentrate vessels, in a system, however, would result in a conductivity that is above or below the expected range and thus triggering the alarm and preventing initiation of the dialysis session Second, the distribution of the chemicals in the acid and bicarbonate concentrates of the invention results in a minimum total volume and weight of concentrates per given volume of final dialysate compared with current commercial packages available. Conventional dialysis systems such as the ones produced by Baxter and Fresenius generally require 3.43 liters of acid and 6.23 liters of bicarbonate concentrate for one 4-hour dialysis treatment. Since a daily dialysis session is typically 90 minutes, conventional system volumes required for daily dialysis are 1.29 and 2.34 liters, respectively. In contrast, the present invention can provide a total concentrate volume of as little as 0.9 liters (2×450 mL bottle) versus a conventional system of 3.63 liters (1.29 L+2.34 L). In other words, the acid and bicarbonate concentrates of the invention are about 4 (3.63/0.9) times more compact in terms of volume compared to conventional systems. Moreover, the nearly saturated acid concentrate provides protection against freezing and dextrose recrystallization, a common problem found in conventional acid concentrate formulations.

Third, the distribution of the chemicals in the acid and bicarbonate concentrates of the invention results in greater control and accuracy of sodium and chloride ion concentrations in the dialysate. One of the problems with the conventional systems is maintaining high level accuracy of sodium and chloride ions. Many physicians prefer +/−2% for these ions. ANSI/AAMI RD-61:2000 standards recommends less than 2.5% variation for sodium. Since the conventional systems involve making a concentrate for sodium bicarbonate (with or without sodium chloride) and then subsequently dilute to final volume, high accuracy cannot be obtained. The concentrate formulations of the present invention are designed to have only small portions of sodium chloride in acid concentrate and have all the rest of the sodium in powder from which is diluted directly. By shifting most of the sodium ions to dry powder, it is now possible to achieve +/−1% accuracy of 90% of sodium chloride and 100% of sodium bicarbonate in the dialysate. Moreover, it is easy to control weights of dry powder components in the concentrate (+/−1%) formulations, thus allowing much higher degree of accuracy in the final solution.

Fourth, both the acid and bicarbonate concentrates of the invention occupy nearly equal volumes and this advantageously allows for identical container design, thus reducing costs of molds and manufacturing processes. Furthermore, identical container design makes it easier for the manufacturer as well as for the user. Since the connection to the machines are identical and mix-up eliminated by color coding, visual label checking and conductivity assurance, the use of the acid and bicarbonate concentrates of the invention to prepare batch dialysate provide the highest degree of quality assurance and safety to the patients.

Finally, by providing citrate ion in the powder form with dry bicarbonate base powder, a number of advantages can be had such as: (1) high accuracy for citrate and sodium ions can be achieved, (2) longer shelf-life for powder will be possible compared with a dissolved citrate ion in acid formulation, (3) possible to use current standard acid concentrate formulations for citrate dialysis, (4) reduce number of additional liquid codes required, and (5) allow simple manufacturing operation for citrate based dialysis formulations.

In the examples below, a procedure is described using a home dialysis machine for preparing a batch dialysate and for preparing a dialysate using a proportioning system. Tables are also provided which list representative acid and bicarbonate concentrate formulations as well as batch dialysate formulations prepared by various combinations of the two concentrates. The selection of a particular combination of acid concentrate and bicarbonate concentrate to prepare a 54.5 L batch of a dialysate formulation having a desired balance of electrolytes is largely dependent on the patient's condition and health needs, and will be prescribed by a physician. The resulting batch of dialysate prepared by mixing the two components in water and diluting the solution to 54.5 L does not require any further manipulations such as pH adjustment. The concentrate containers are designed to provide chemicals for batch volumes ranging from 40 liters to 60 liters. The concentrate containers can also be designed to provide continuous streams of acid and base concentrates containing citrate to a proportioning system and to multiple treatment delivery systems.

EXAMPLE 1

Preparation of Batch Dialysate

All chemical reagents employed in preparing the concentrates are USP grade unless otherwise indicated.

(a) Preparation of batch quantity acid concentrate unit. In making the acid concentrate, dextrose is dissolved in a predetermined amount of water with continuous stirring at room temperature, e.g. 70° F. Thereafter, the remaining salts and acetic acid are slowly added to the stirring of the solution and the solution volume is raised to a final volume, e.g., 399 mL, with appropriate amounts of water to produce the acid concentrate. If desired, the concentrate may be sterilized by filtration through a sterile 0.2 micron filter or by autoclaving. The acid concentrate is then poured into a batch quantity vessel such as the one described in the above-referenced Treu et al. patent, and the vessel sealed.

(b) Preparation of batch quantity dry bicarbonate unit. In making the dry bicarbonate concentrate, 280.3 grams of NaCl, and 160.2 grams of $NaHCO_3$, are thoroughly mixed with 14 grams of sodium citrate. The resulting 454.4 gram powder mixture is then placed into a batch quantity vessel such as the one described in the above-referenced Treu et al. patent, and the vessel sealed. Alternatively, the salts are simply added to the batch quantity vessel and sealed. No additional mixing in the vessel is required because all of them are completely dissolved in the dialysate tank and thus uniformly distributed.

(c) Preparation of batch dialysate. A 54.5 liter dialysate chemical solution tank is installed in a dialysis machine. The tank has a chemical loading platform that acts as a means for receiving the dialysate chemicals and for introducing the chemicals into the tank. The tank is filled up to the level of the chemical loading platform, or roughly 50 percent of capacity. The chemical loading platform has a slanted shelf which is in fluid communication with the interior of the tank. The contents of the vessels containing the batch quantity dry bicarbonate chemicals and the batch quantity liquid acid concentrate are gradually released from the vessels by gravity and are deposited onto the slanted shelf of the loading platform. The vessels can be either manually opened or automatically opened (in the manner described in the above-referenced Treu et al. patent), depending on the construction of the tank and loading platform. A nozzle sprays reverse-osmosis filtered water onto the slanted shelf to disperse the chemicals into the interior of the tank. The tank is then filled completely with RO water. The solution is mixed by swirling the fluid in the tank, accomplished by introducing the RO water into the bottom of the tank generally parallel to the side of the tank, and by withdrawing solution from the bottom of the tank and reintroducing it at the top of the tank in a turbulent manner with a sprayer.

The flow path of the dialysate when it is withdrawn from the bottom of the tank and reintroduced at the top of the tank includes a conductivity sensor. The conductivity sensor sends conductivity readings to a central processing unit controlling the operation of the machine. When the conductivity readings meet an expected value for the particular dialysate formulation, the solution is deemed mixed and the mixing process ceases. The dialysis session then commences according to well known techniques.

Table 5 lists representative formulation ranges for different liquid acid concentrates. The particular formulation to be used for preparation of a batch of dialysate depends upon the medical condition of the patient, and will be prescribed by a physician. The conductivity of acid concentrate when diluted to the required volume by itself (without powder) will range between 2-3 mS/cm.

Table 6 shows representative formulation ranges for different batch quantity dry bicarbonate chemicals formulations. The dialysate solution is prepared by mixing one of the formulations from Table 5 with one of the formulations from Table 6. As was the case with Table 5, the particular formulation to be selected from Table 6 depends on the medical condition of the patient, and will be prescribed by the patient's physician. This formulation is for dilution to a 54.5 liter batch of dialysate. Again, the precise quantities of the salt and bicarbonate may vary depending on the final volume of dialysate that is prepared.

Since there are 16 representative acid concentrate formulations and 6 representative bicarbonate formulations, there are 96 possible final dialysate combinations.

EXAMPLE 2

Preparation of Concentrates for a Proportioning System

All chemical reagents employed in preparing concentrates are USP grade unless otherwise indicated.

(a) Preparation of bulk quantities of an acid concentrate. This is generally done in a large vessel (50 liters to 25,000 liters). In making an acid concentrate, dextrose is dissolved in a predetermined amount of water with continuous stirring at room temperature, e.g. 70° F. Thereafter, the remaining salts and acetic acid are slowly added while the mixture is stirred. The mixture is raised to a final chosen volume with an appropriate amount of water to produce the acid concentrate. If desired, the concentrate so obtained can be sterilized by filtration through a sterile 0.2 micron filter or by autoclaving. The acid concentrate is then transferred into filling machines and filled into a batch quantity vessel that is commercially available (starting from 100 mL container to 55 gallon drum). The containers are then sealed and transported to customers.

(b) Preparation of batch quantities of a dry bicarbonate concentrate. In making a bulk dry bicarbonate concentrate, appropriate quantities of NaCl, $NaHCO_3$ and sodium citrate are metered into containers or bags of appropriate sizes. The user is required to transfer the whole contents of the dry chemicals into a mixing vessel before use and completely dissolve the chemicals. Alternately, the manufacturer can package the concentrates in a way similar to how the bulk acid concentrates are packaged as described in section (a) above.

(c) Final dialysate generation. In case of a proportioning system, the acid concentrate and the bicarbonate concentrate are supplied to the dialysis machine in ready-to-dispense containers (either supplied by the concentrate manufacturer or by the machine manufacturers) along with a water supply. Generally, the dialysis machine has the capacity to adjust appropriately to arrive at a correct proportioning ratio so that a desirable final dialysate is produced.

The examples described above are by way of illustration and are not meant to limit the scope of the present invention. It is expected that certain changes, substitutions and modifications of the present invention will be apparent to a person skilled in the art to which the present invention pertains, without departing from the spirit of the present invention.

TABLE 5

Formulation table for batch quantity acid concentrate
Acid "A" codes - Acid formulations for "Citrate Containing Base" Formulations

| Acid Code | mEq/l Na+ | mEq/l K+ | mEq/l Ca++ | mEq/l Mg++ | mg/dl Dextrose | mEq/l Acetate- | mEq/l Cl- |
|---|---|---|---|---|---|---|---|
| 1A01 | 15 | 3 | 3.0 | 0.75 | 200 | 4 | 21.75 |
| 1A02 | 15 | 3 | 2.5 | 0.75 | 200 | 4 | 21.25 |
| 1A03 | 15 | 2 | 3.0 | 0.75 | 200 | 4 | 20.75 |
| 1A04 | 15 | 2 | 2.5 | 0.75 | 200 | 4 | 20.25 |
| 1A05 | 15 | 3 | 3.5 | 0.75 | 200 | 4 | 22.25 |
| 1A06 | 15 | 2 | 2.5 | 1.50 | 200 | 4 | 21.00 |
| 1A07 | 15 | 3 | 3.5 | 1.00 | 200 | 4 | 22.50 |
| 1A08 | 15 | 2 | 3.5 | 0.75 | 200 | 4 | 21.25 |
| 1A09 | 15 | 2 | 2.5 | 1.00 | 200 | 4 | 20.50 |
| 1A10 | 15 | 2 | 0.0 | 1.00 | 200 | 4 | 18.00 |
| 1A11 | 15 | 2 | 3.0 | 1.00 | 200 | 4 | 21.00 |
| 1A12 | 15 | 2 | 3.0 | 1.00 | 0 | 4 | 21.00 |
| 1A13 | 15 | 2 | 2.5 | 1.00 | 0 | 4 | 20.50 |
| 1A14 | 15 | 1 | 2.5 | 1.00 | 200 | 4 | 19.50 |
| 1A15 | 15 | 1 | 3.0 | 0.75 | 200 | 4 | 19.75 |
| 1A16 | 15 | 0 | 2.5 | 0.75 | 200 | 4 | 18.25 |

TABLE 6

Formulation table for batch quantity citrate-containing bicarbonate concentrate

| Citrate-Containing Code # | Sodium Chloride NaCl Gms | Sodium Bicarbonate $NaHCO_3$ gms | Sodium Citrate $C_6H_5Na_3O_7$ Gms | Total Weight gms | Bicarbonate $HCO_3$ mEq/L | Sodium Na mEq/L | Chloride Cl mEq/L | Citrate $C_6H_4O_7$ mEq/L | Total Base with Citrate & Acetate mEq/L |
|---|---|---|---|---|---|---|---|---|---|
| 1B11 | 280.3 | 167.1 | 8.7 | 456.1 | 36.5 | 127 | 88 | 2.5 | 39 |
| 1B12 | 283.5 | 144.2 | 8.7 | 436.4 | 31.5 | 123 | 89 | 2.5 | 34 |

TABLE 6-continued

Formulation table for batch quantity citrate-containing bicarbonate concentrate

| Citrate-Containing Code # | Sodium Chloride NaCl Gms | Sodium Bicarbonate NaHCO$_3$ gms | Sodium Citrate C$_6$H$_5$Na$_3$O$_7$ Gms | Total Weight gms | Bicarbonate HCO$_3$ mEq/L | Sodium Na mEq/L | Chloride Cl mEq/L | Citrate C$_6$H$_4$O$_7$ mEq/L | Total Base with Citrate & Acetate mEq/L |
|---|---|---|---|---|---|---|---|---|---|
| 1B13 | 267.5 | 167.1 | 8.7  | 443.4 | 36.5 | 123 | 84 | 2.5 | 39 |
| 1B14 | 280.3 | 160.2 | 14.0 | 454.5 | 35.0 | 127 | 88 | 4   | 39 |
| 1B15 | 283.5 | 137.4 | 14.0 | 434.8 | 30.0 | 123 | 89 | 4   | 34 |
| 1B16 | 267.5 | 160.2 | 14.0 | 441.7 | 35.0 | 123 | 84 | 4   | 39 |

Note:
The quantities in gms represent typical formulations for use with a batch system of 54.5 liters final volume. These weights will be proportionately more or less for different batch volumes and for proportioning system.

What is claimed:

1. A method of making a dialysate and circulating the dialysate comprising:
   (a) providing a dialysis apparatus comprising a conductivity sensor for measuring conductivity of a solution and a dialyzer having a dialysate side and a blood side;
   (b) providing a dry base concentrate comprising a citrate, bicarbonate and a salt, wherein a sodium contribution of the dry base concentrate to the dialysate ranges from 100 to 150 mEq/L and wherein ratio of bicarbonate (mEq/L) to citrate (mEq/L) in the dry base concentrate ranges from 50:1 to 15:8;
   (c) providing an acid concentrate comprising an acid selected from the group consisting of acetic acid, citric acid and lactic acid, wherein (i) a sodium contribution of the acid concentrate to the dialysate ranges from 10 to 20 mEq/L, (ii) the combination of the sodium contributions of the dry base concentrate and the acid concentrate to the dialysate ranges from 125 to 150 mEq/L and (ii) the base concentrate and the acid concentrate are separated into separate containers;
   (d) mixing said base concentrate, said acid concentrate, and water so as to produce dialysate;
   (e) measuring conductivity of said dialysate with said conductivity sensor; and
   (f) circulating said dialysate to said dialysate side of said dialyzer if said conductivity of said dialysis solution ranges from between about 12.5 and about 15.7 mS/cm and not circulating the dialysate if said conductivity falls outside of said conductivity range.

2. The method of claim 1, wherein said citrate is selected from the group consisting of citric acid, a salt of citric anion, and a partial ester of citric anion.

3. The method of claim 1, wherein said citrate is trisodium citrate, disodium hydrogen citrate or monosodium dihydrogen citrate.

4. The method of claim 3, wherein the base concentrate is in a first vessel and the acid concentrate is in a second vessel, the first and second vessels containing an amount of said base and acid concentrates for preparation of a dialysate for treatment of a single patient.

5. The method of claim 1, wherein said acid in said acid concentrate is acetic acid.

6. The method of claim 1, wherein said salt is selected from the group consisting of sodium chloride, potassium chloride, calcium chloride and magnesium chloride.

7. The method of claim 1, wherein said citrate is provided in a quantity to provide a final concentration in said dialysate from about 1 to about 8 mEq/L.

8. The method of claim 1, wherein said bicarbonate is provided in a quantity to provide a final concentration in said dialysate from about 15 to about 50 mEq/L of said bicarbonate.

9. The method of claim 1, wherein said salt is provided in a quantity to provide a final concentration in said dialysate from about 1.5 to about 150 mEq/L.

10. The method of claim 1, wherein said acid in said acid concentrate being provided in a quantity sufficient to provide a final concentration in said dialysate of between about 1 to about 8 mEq/L.

11. The method of claim 1, wherein the base concentrate comprises:
    (a) sodium bicarbonate;
    (b) sodium citrate, wherein molar ratio of sodium bicarbonate to sodium citrate ranges from 50:1 to 15:9; and
    (c) sodium chloride in an amount sufficient to provide final concentration in the said dialysate of sodium in the range of 125 to 150 mEq/L when the base concentrate and acid concentrate are mixed with water.

12. The method of claim 1, wherein the base concentrate comprises:
    (a) bicarbonate in sufficient amount to provide about 36.5 mEq/L in the final dialysate;
    (b) sodium in sufficient amount to provide about 127 mEq/L in the final dialysate;
    (c) chloride in sufficient amount to provide about 88 mEq/L in the final dialysate; and
    (d) citrate in sufficient amount to provide about 2.5 mEq/L in the final dialysate.

13. The method of claim 1, wherein the base concentrate comprises:
    (a) bicarbonate in sufficient amount to provide about 31.5 mEq/L in the final dialysate;
    (b) sodium in sufficient amount to provide about 123 mEq/L in the final dialysate;
    (c) chloride in sufficient amount to provide about 89 mEq/L in the final dialysate; and
    (d) citrate in sufficient amount to provide about 2.5 mEq/L in the final dialysate.

14. The method of claim 1, wherein the base concentrate comprises:
    (a) bicarbonate in sufficient amount to provide about 36.5 mEq/L in the final dialysate;

(b) sodium in sufficient amount to provide about 123 mEq/L in the final dialysate;
(c) chloride in sufficient amount to provide about 84 mEq/L in the final dialysate; and
(d) citrate in sufficient amount to provide about 2.5 mEq/L in the final dialysate.

15. The method of claim 1, wherein the base concentrate comprises:
(a) bicarbonate in sufficient amount to provide about 35 mEq/L in the final dialysate;
(b) sodium in sufficient amount to provide about 127 mEq/L in the final dialysate;
(c) chloride in sufficient amount to provide about 88 mEq/L in the final dialysate; and
(d) citrate in sufficient amount to provide about 4 mEq/L in the final dialysate.

16. The method of claim 1, wherein the base concentrate comprises:
(a) bicarbonate in sufficient amount to provide about 30.0 mEq/L in the final dialysate;
(b) sodium in sufficient amount to provide about 123 mEq/L in the final dialysate;
(c) chloride in sufficient amount to provide about 89 mEq/L in the final dialysate; and
(d) citrate in sufficient amount to provide about 4 mEq/L in the final dialysate.

17. The method of claim 1, wherein the base concentrate comprises:
(a) bicarbonate in sufficient amount to provide about 35 mEq/L in the final dialysate;
(b) sodium in sufficient amount to provide about 123 mEq/L in the final dialysate;
(c) chloride in sufficient amount to provide about 84 mEq/L in the final dialysate; and
(d) citrate in sufficient amount to provide about 4 mEq/L in the final dialysate.

18. The method of claim 2, wherein said citrate is citric acid and said citric acid is separated from said bicarbonate.

19. The method of claim 18, wherein the base concentrate is contained in a vessel for preparation of a batch of dialysis solution for treatment of single patient and said salt is present as a layer deposited in the vessel between said citric acid and said bicarbonate.

20. The method of claim 18, wherein said citric acid in the base concentrate is in the form of tablets.

21. The method of claim 20, wherein the tablets are coated with dextrose and sodium chloride.

22. The method of claim 1, wherein prior to step (c), the base concentrate and acid concentrate are separately dissolved into water to form aqueous base and acid concentrates.

23. The method of claim 22, wherein the aqueous base and acid concentrates are metered to a metered volume of water so as to produce said dialysis solution on-line on a continuous basis.

* * * * *